(12) United States Patent
Fling et al.

(10) Patent No.: US 7,574,912 B2
(45) Date of Patent: Aug. 18, 2009

(54) COLLAPSIBLE LIQUID LEVEL MEASUREMENT DEVICE WITH ATTACHMENT

(76) Inventors: William F. Fling, 48501 E. Buckhorn Cove Rd., Little River, CA (US) 95456; John J. Fling, 48501 E. Buckhorn Cove Rd., Little River, CA (US) 95456

( * ) Notice: Subject to any disclaimer, the term of this patent is extended or adjusted under 35 U.S.C. 154(b) by 0 days.

(21) Appl. No.: 11/801,433

(22) Filed: Jun. 19, 2007

(65) Prior Publication Data
US 2007/0234798 A1    Oct. 11, 2007

Related U.S. Application Data

(63) Continuation-in-part of application No. 10/961,389, filed on Oct. 8, 2004, now abandoned.

(51) Int. Cl.
*G01F 23/30* (2006.01)
(52) U.S. Cl. .................. 73/305; 73/315; 73/290 R; 73/322.5; 340/624
(58) Field of Classification Search .................. 73/313, 73/315, 290 R, 305, 322.5; 340/623, 624
See application file for complete search history.

(56) References Cited

U.S. PATENT DOCUMENTS 2,069,793 A * 2/1937 Watson ........................ 73/315
2,592,929 A * 4/1952 Matchett ...................... 73/313
4,064,754 A * 12/1977 Frey ............................. 73/313
4,154,103 A * 5/1979 Fling ............................ 73/315
4,802,363 A * 2/1989 Fling et al. ................... 73/315
4,833,919 A * 5/1989 Saito et al. ................... 73/313
5,054,319 A * 10/1991 Fling ............................ 73/319

* cited by examiner

*Primary Examiner*—Hezron Williams
*Assistant Examiner*—Samir M Shah
(74) *Attorney, Agent, or Firm*—Lynn & Lynn

(57) ABSTRACT

A liquid level measuring device includes an elongate handle and an elongate frame arranged in telescoping relationship. The frame is movable between a collapsed position for storage and an extended position for usage. A float is movable lengthwise along the elongate frame. A control rod extends lengthwise in the elongate frame and through a passage in the float. The control rod controls movement of the float relative to the elongate frame. An actuator actuates the control arm to move the float from the locked position to the unlocked position in response to a downward pressure between a lower end of the elongate frame and a bottom surface of the container so that the float is free to seek the liquid level in the container and to move the float from the unlocked position back to the locked position when the downward pressure is released.

3 Claims, 5 Drawing Sheets

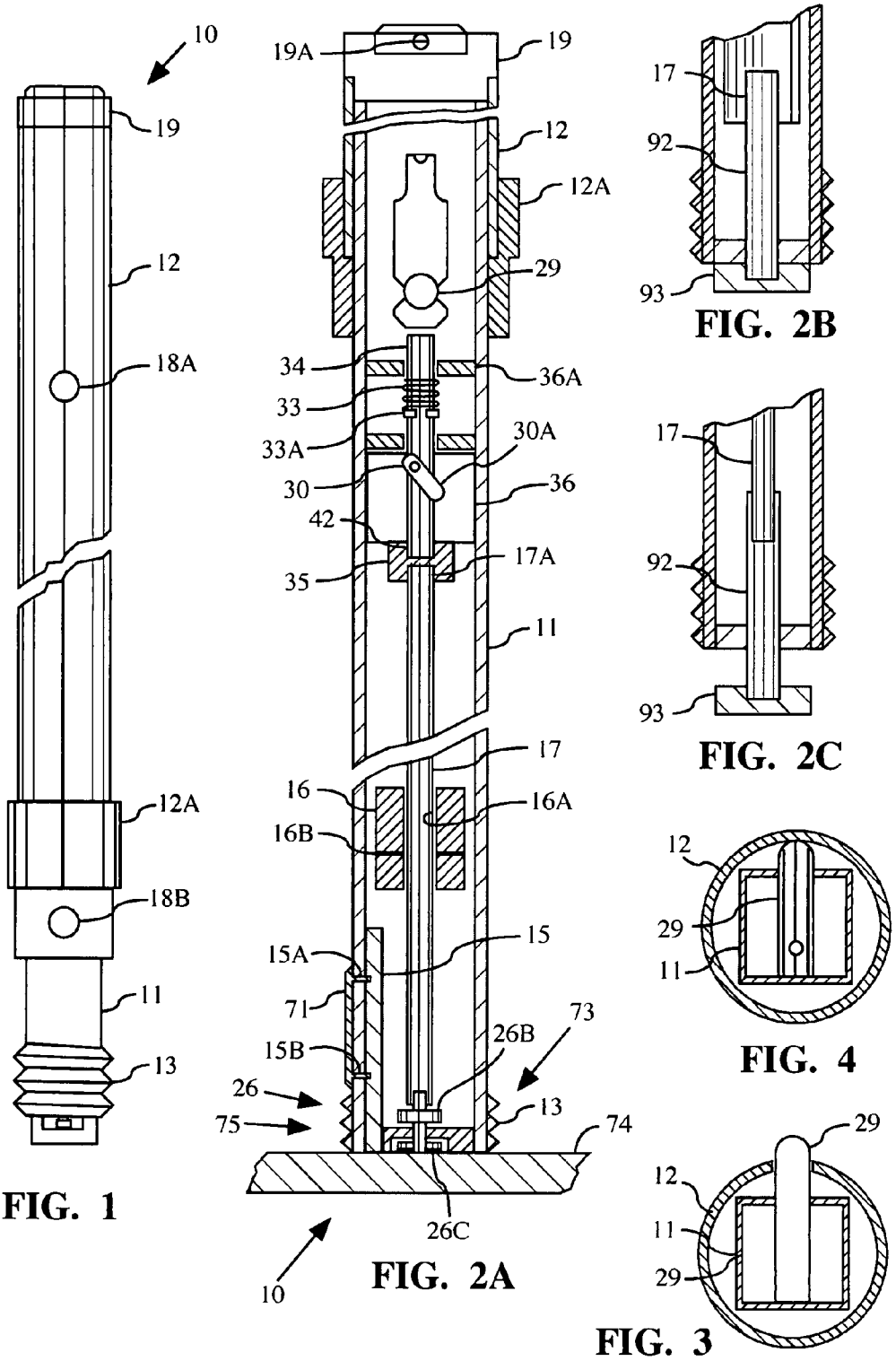

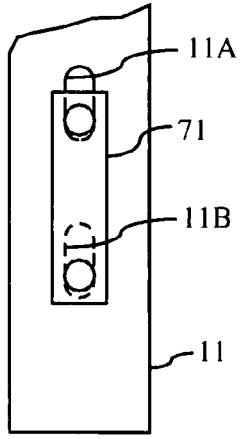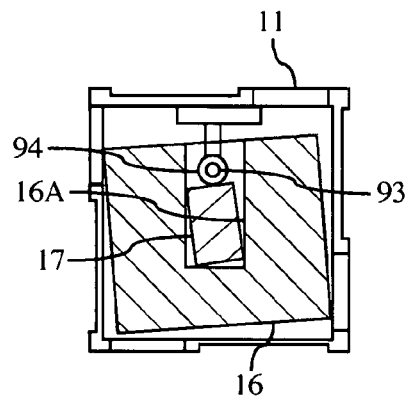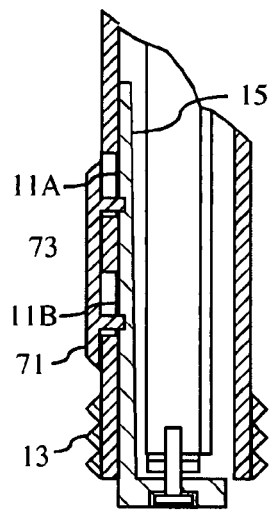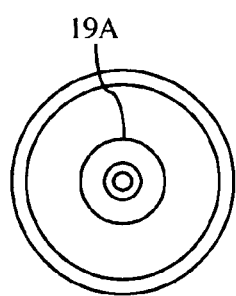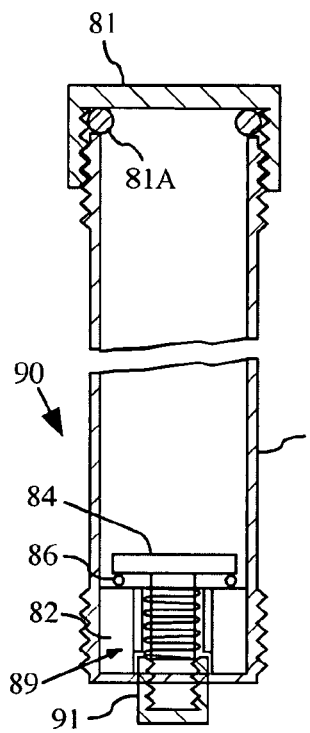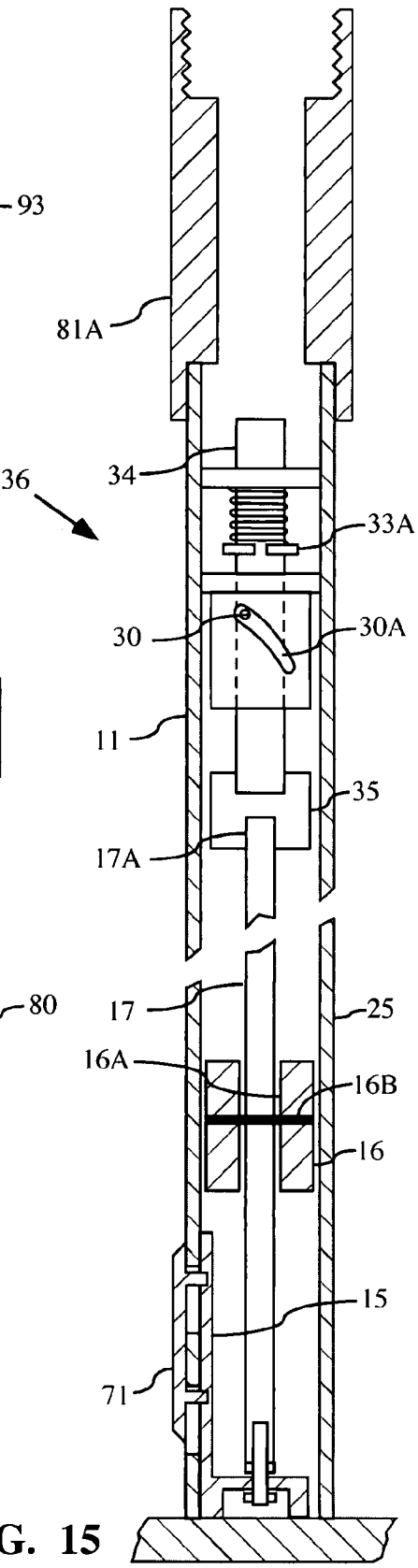
FIG. 12
FIG. 13
FIG. 14
FIG. 16
FIG. 17
FIG. 15

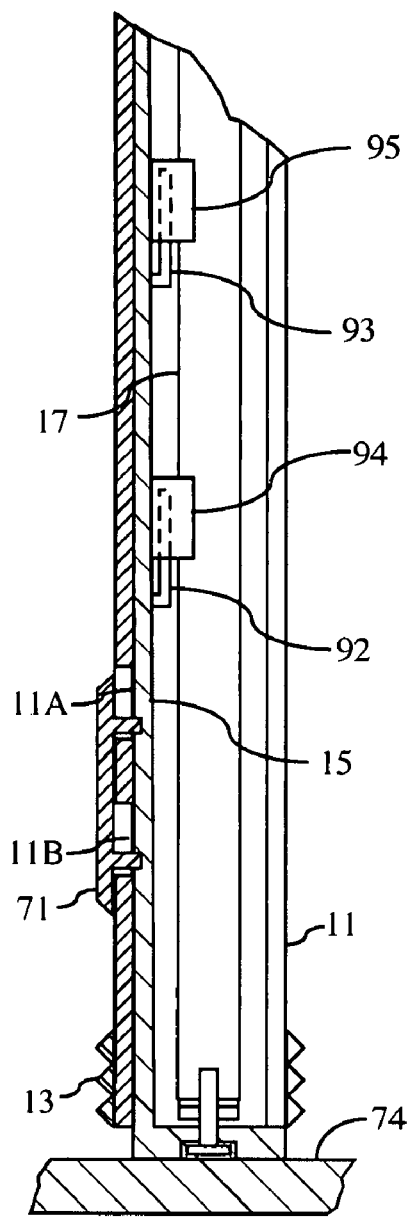
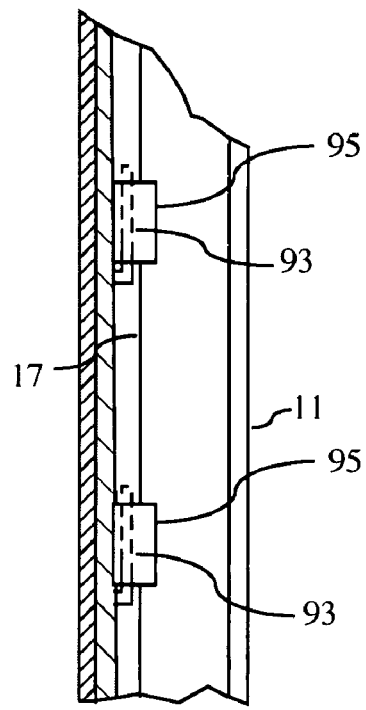
FIG. 24
FIG. 23
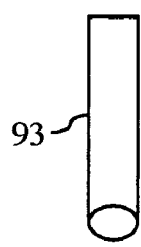
FIG. 25
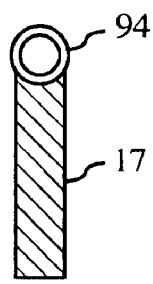
FIG. 26

COLLAPSIBLE LIQUID LEVEL MEASUREMENT DEVICE WITH ATTACHMENT

CROSS REFERENCE TO RELATED APPLICATION

This a continuation in part of applicants' application Ser. No. 10/961,389, filed Oct. 8, 2004 now abandoned.

BACKGROUND OF THE INVENTION

1. Field of the Invention

The present invention relates generally to the measurement of the depth of a quantity of liquid in a tank, container or the like, and, more particularly, to an improved liquid depth measurement device having a water level indicator and a fluid sampling device.

2. Description of the Prior Art

There are many instances in which it is desirable or essential to be able to measure the depth of a fluid in large under ground and above ground storage tanks, container, or the like to determine the volume of the fluid contained therein. Large underground or above-ground bulk storage tanks are typically situated at gasoline service stations, convenience stores, factories, office buildings, truck stops, etc. In addition, the same requirements apply to numerous smaller tanks and containers. Dipsticks are commonly used primarily as back up to automated leak detection and inventory control systems that are mandatory for the large bulk storage tanks or as the primary method for the measurement of smaller tanks and containers.

The most frequently used device for this purpose is the common wooden dip stick which is inserted into the tank, container or the like until its lower end strikes the bottom after which the gauge is raised up and the fluid depth is determined by noting the upper extent of the wetted portion on the pole (wet line). A typical dipstick has lines of demarcation marked off along its length so that the liquid depth can be determined after the dipstick is withdrawn from the tank so that the location of the wet line can be seen.

Wooden gauge dipsticks suffer from many deficiencies that make them less than satisfactory for accuracy, durability or dependability. They do not meet current stringent requirements for accountability for tank leakage and product inventory control. For example, scales are neither precise nor protected and thus are subject to wear and tear with repeated use. The unprotected blunt end of the wood sticks damages the bottom of the tanks through pinning action and cause eventual erosion of the tank bottoms. Wood sticks are subject to splintering, breakage and warping requiring frequent replacement. The reliance on the wet line as the indicator of product level is inaccurate and at best is an approximate reading. The wet line is the result of residual fluid deposited on the scale at the time of stick submersion and withdrawal from the tank and is subject to rapid evaporation. The scales are difficult to read in wet weather conditions and night tank readings. These conditions require the need for multiple readings and are time consuming. Wood sticks when inserted in tanks rapidly are subject to splashing that may result in inaccurate measurements.

SUMMARY OF THE INVENTION

The present invention relates to a telescopic mechanized device for the measurement of fluid products contained in below-ground and above-ground tanks and containers. An attachment is provided for measuring the amount of water in the tanks or containers. A handle member forming the upper portion of the device within which an enclosed tubular housing having a plurality of openings in it side walls providing ready fluid communication from the outside to the tubular central space. A control bar extends along the inner cavity of the tubular housing and is pivotally mounted to swing from a first position extending laterally along a diameter of the housing to a second position closely adjacent to the housing interior wall. A float of outer dimensions substantially less than the internal diameter of the tubular housing has a centered longitudinal slot that fits over the control bar and is relatively free for movement longitudinally within the frame section when the control bar is in activated its first position. When the control bar is in its second locked position, the float becomes wedged against the control bar and is constrained against movement relative to the control bar and frame section. The control bar is secured to the frame section by actuators at both ends of the housing and controls the movement of the control bar between its first and second positions. Markings inscribed on the surfaces of the lower frame indicate the respective distance of the float from the bottom or interval end of the frame housing, and in that way serves as a direct measurement of the fluid level within the tank or container.

The invention also includes an attachment to the collapsible liquid measuring device that may be used as an alternative to the paste method for measuring water that collects at the bottom of the tank or container. The attachment is identical in construction and function in a short length version without the handle for mounting on the frame of the full-size-measuring device. With the measuring device in the fully extended mode and the water sampling device attached, the entire unit is lowered into the tank or container. The downward pressure on the device actuates the water attachment unit thus providing the desired measurement of water contents in the tank or container. A further enhancement of the liquid measuring device is a product sampler secured to the lower end portion of the frame section. The product sampler includes an open-end tube with a valve on its lower end. The valve is activated on contract with the tank or container bottom to admit fluid. End caps are threaded onto the sampler tube to maintain the sampled fluid for storage and shipment.

BRIEF DESCRIPTION OF THE DRAWINGS

FIG. 1 illustrates a liquid level measuring device according to the invention in a collapsed mode with a frame section extending into a handle and secured by a snap button.

FIG. 2A is a cross sectional view showing the present invention in an extended mode with a float and float control assembly arranged to measure liquid levels.

FIGS. 2B and 2C are cross sectional views showing means for activating a control bar to lock a float in a position in the frame section to indicate a liquid level.

FIG. 3 is a cross sectional view of snap button in its locked position securing the handle to the frame section.

FIG. 4 is an end view of the snap button in a depressed position to allow the frame section to be moved between the collapsed and extended modes in the handle.

FIG. 12 is a fragmented view of the back portion of the slave piston in the unlocked mode.

FIG. 13 is a cross sectional view that shows the position of the frame section relative to the control bar and the float in the locked position.

FIG. 14 is a cross sectional view showing the slave piston assembly in the locked mode when withdrawn from the tank or container.

FIG. 15 is a cross sectional view of a water level indicator attachment that may be included in the invention.

FIG. 16 is a top view of the handle leveling bubble.

FIG. 17 is a cross sectional view of the liquid sampler attachment in the inactive mode.

FIG. 23 is a cross sectional view showing the position of the frame section to the control bar in the activated mode and showing interaction of the control bar sleeves and the slave pins.

FIG. 24 is a fragmentary view showing the position of the sleeves and control pins when the control bar is in the deactivated mode.

FIG. 25 illustrates a slave pin that may be included in the invention.

FIG. 26 illustrates attachment of a sleeve to the control bar.

DETAILED DESCRIPTION OF THE INVENTION

Turning now to the drawings and particularly to FIGS. 1, 2 and 3, a liquid level measuring device 10 includes an elongated tubular handle 12 and an elongated frame section 11. The handle 12 and the frame section 11 are connected in a telescopic relationship with the frame section 11 extending inside the handle 12 to form a rigid assembly that may be arranged in either an extended configuration for usage or a collapsed configuration for use in measuring liquid levels. It is a primary aim of the device described herein to measure the level of fluids in tanks or containers so that the fluid volume can be determined.

The liquid level measuring device 10 according to the invention may be advantageously employed for measuring fluids of great variety in containers and tanks such as, for example, containers for domestic heating oil, industrial fluid storage tanks, military storage facilities, gasoline stations, and the like. It is also considered within the spirit of this invention to make the measurement device small-sized for such uses as measuring depth in drums, barrels, vehicle tanks, aircraft tanks, and recreational power boat tanks, for example.

Figure 5:
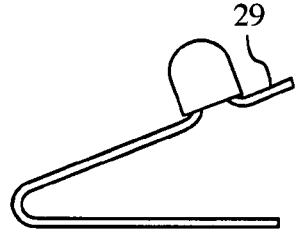
FIG. 5 is a side view of the snap button.
Figure 6:
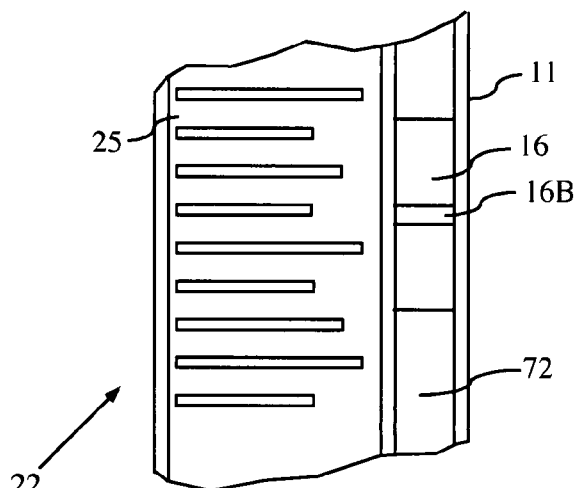
FIG. 6 is a front view of the frame section showing the float's wet line adjacent a scale.

Referring to FIGS. 1 and 2A, the liquid level measuring device 10 is shown as a straight, elongated structure having an overall length such that when one end is resting on the bottom 74 of a tank the opposite end will extend outwardly of the tank fill tube a sufficient amount ready for hand manipulation. The liquid level measuring device 10 includes a handle 12 with a cap 19 having a leveling bubble 19A therein to indicate the local vertical attached at the top of the handle as shown in FIGS. 1 and 2A. The frame section 11 has a plurality of slot openings 72A (FIG. 6) arranged in its sidewalls to provide ready fluid communication from the outside to the frame's central space. The handle 12 and frame 11 sections are connected in a telescopic relationship to form a rigid elongated device 10. The handle 12 serves as an extension of the frame section 11 and accommodates storage in confined spaces. In addition, the liquid level measuring device 10 can be used as a non-collapsible single device and can be made in various sizes and configurations to accommodate various sizes and configurations of tanks, drums and containers.

FIG. 1 shows the liquid level measuring device 10 in the collapsed mode. FIG. 2A shows the liquid level measuring device 10 in its extended mode. As shown, the collapsed device 12 is extended by depressing a high-tension snap button 29 that protrudes from a hole 18A located near the upper end of handle 12. As the handle 12 and the frame section 11 are extended, the snap button 29, as shown in FIG. 23, located internally to the surface to the upper end of the frame section 11, is depressed and slides under the inner surface 12B of the handle 12 until it encounters hole 18A of collar 12A. At this point the snap button 29 protrudes into hole 18B and secures the device 10 in the extended mode. To collapse the device, snap button 29 is depressed, and the frame section is slid into the handle 12 until the snap button 29 engages hole 18A of the handle, thus securing the collapsed mode.

Figure 11:
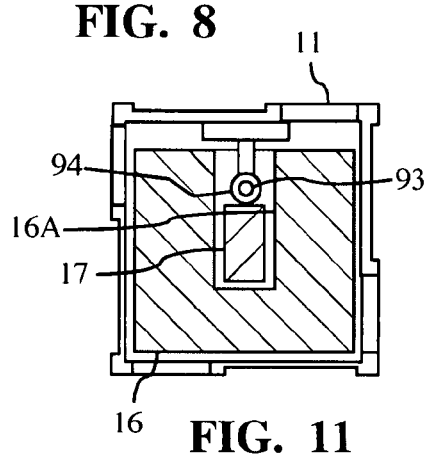
FIG. 11 is a cross sectional view that shows the position of the frame section relative to the control bar and the float in the unlocked mode.
Figure 18:
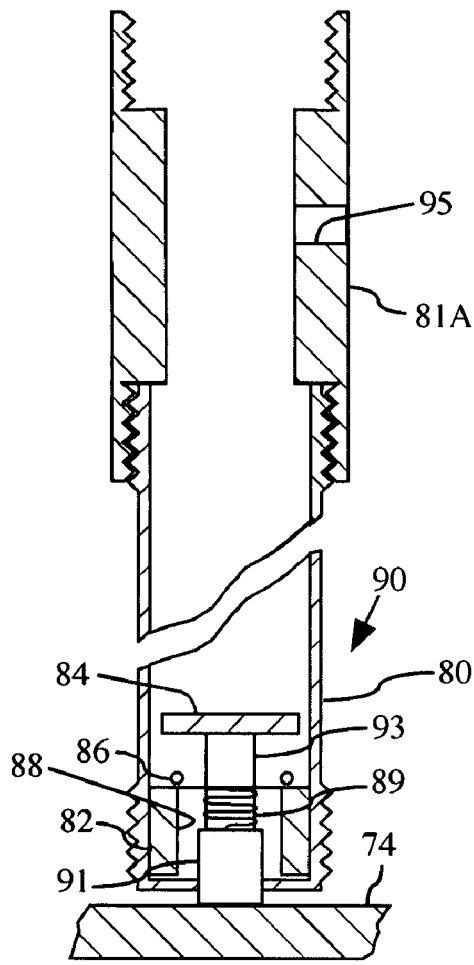
FIG. 18 is a cross sectional view of the fluid sampler attachment connected to the frame section with the piston depressed to accept a liquid fluid sample.
Figure 20:
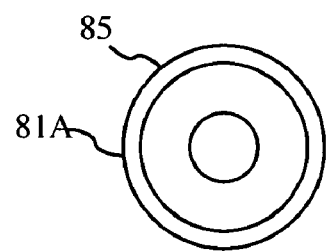
FIG. 20 is a top plan view of the end cap of FIG. 19.
Figure 21:
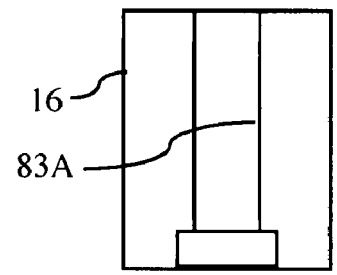
FIG. 21 is a cross sectional view of the float showing the lengthwise slot.
Figure 19:
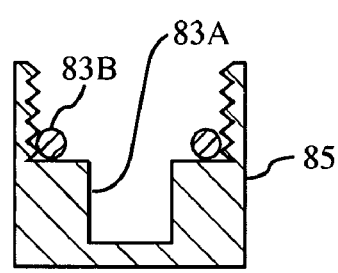
FIG. 19 is a cross sectional view of a bottom end cap for the liquid sampler of FIGS. 17 and 18.
Figure 22:
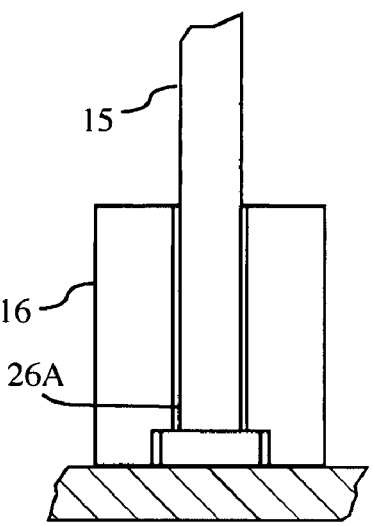
FIG. 22 is a cross sectional view showing the float seated on the slave piston at the lowest possible end of the frame section.

Turning to FIG. 1, an elongated control bar 17 extends along the inner cavity of the frame section 11. Referring to FIGS. 2A, 11 and 13, a float 16 of outer dimensions substantially less than the internal dimensions of the frame section 11 has a centered longitudinal passage 16A which fits over the control bar 17 and is relatively free for movement longitudinally within the frame section 11 when the control bar is in its first position. When the control bar is in a second position, the float becomes wedged against the control bar 17 and is constrained against movement relative to the control bar 17 and frame section 11.

The control bar 17 is pivotally secured to the frame section 11 top section by an actuator 36 that controls the movement of the control bar 17 in conjunction with a slave piston assembly 73 attached to the lower end 75 of the frame section 11. Referring to FIGS. 11, 13, and 23-26, the control bar 17 is further secured to the frame section 11 by slave pins 92 and 93 that are spaced along the length of the frame section 11 along with matching sleeves 94 and 95 of the control bar to assure rigidity. Two pins 92 and 93 are shown, however, additional pins and corresponding sleeves may be used to secure the control bar 17 to the frame 11. As the control bar 17 moves in the frame 11 the sleeves 94 and 95 on the control bar 17 slide on the slave pins 92 and 93 and thus assure rigidity throughout the movement of the control bar 17

The means for selectively adjusting the control bar 17 position will now be described. A housing 36 has a cylindrical end with an open bottom of such dimensions as to permit shaft 34 to move in an upward or downward motion easily therein. A guide pin 30 is embodied in the shaft 34 and is free to move within a guide slot 30A provided in the wall of the housing 36. As shown in FIGS. 2A and 15, the guide slot 30A makes an angle of about 45° with the lengthwise axis of the housing 36 such that lengthwise movement of the shaft 34 in the housing 36 engages the guide pin 30 with edges of the guide slot 30A and causes the shaft 34 to rotate in the housing 36. A collar 35 is attached to the end of the shaft 34 to provide seating for the upper end 17A of the control bar 17 to connect the control bar 17 to the shaft 34 so that rotating the shaft 34 also rotates the control bar. A coil spring 33 inserted over the shaft 34 presses upwards against the top end of the housing body 36A with the bottom of the spring 33 being held in position by the snap ring 33A.

The slave piston means 73 affixed to the bottom end of the lower shaft section 11 serves as the other component for adjusting the control bar 17 position. Guide slots 11A, and 11B, are provided in the bottom side wall of the frame section 11 whereby the slave piston 73 is secured to the frame by mating the piston 26 to the back plate 71 with rivets 15A, and 15B, and spacers 24A, and 24B. In use, the liquid level measuring device 10 is extended from the collapsed to fully extended mode (FIGS. 1 and 2) by depressing the snap ring 29 and pulling the frame section 11 from the handle 12 until the snap ring resurfaces through the handle's hole 18A and thus secures both segments of the device 10. The extended device is then inserted in the tank or container until it contacts the bottom 74 of the vessel were the device is aligned using the alignment bubble 19A to assure the local vertical position alignment of the device 10 to the tank being measured. Reference is now made to FIG. 13, whereas it is shown that in use, the control bar 17 adjusting means 36 and 73 normally rest with the control bar locked against the float 16 and the internal wall of the frame section 11. This force is the result of the reaction of coil 33 exerting a downward pressure on the shaft 34, which in turn presses against the control arm 17.

Reference is now made to FIG. 11, which shows the control arm 17 in the open position in relationship to the float 16 and the inner walls of the frame section 11. As downward pressure is applied to the liquid level measuring device 10, the slave piston means 73 at the bottom of the device is activated when contact is made with the tank bottom. At this time the piston 26 of the slave piston means moves in an upward motion on spacers 24A and 24B, within slots 11A, and 11B, which in turn limit the piston travel length on the frame section. The control arm 17 lower end is connected to the piston 26 through hole 26A with a washer 26B and a snap ring 26C. The upward motion of the control arm forces the shaft 36 within the housing 36 to rotate on the guide pin 30 in guide slot 30A compressing coil spring 33 against the upper edge of the housing 36. The control arm assumes a maximum of a 90-degree angle (Reference FIG. 13) and permits the float 16 to move freely within the frame section to seek the level of the fluid in the tank.

Figure 7:
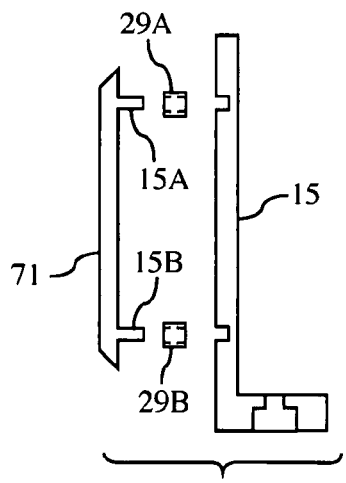
FIG. 7 is an exploded front elevation view of components of a slave piston assembly included in the float control assembly.
Figure 8:
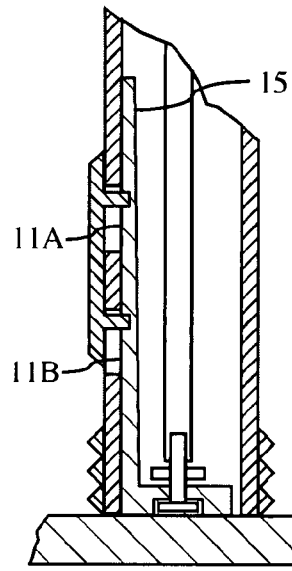
FIG. 8 is a cross sectional view of the slave piston assembly in an activated mode contacting with a tank bottom.
Figure 9:
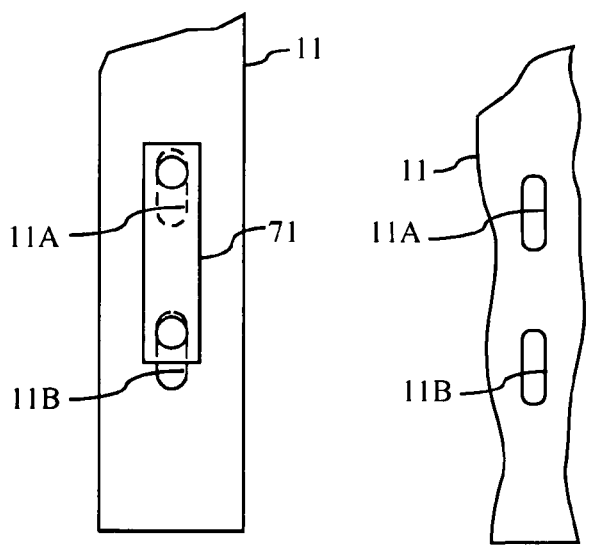
FIG. 9 is a fragmented view of the back portion of the slave piston in the activated mode.
Figure 10:
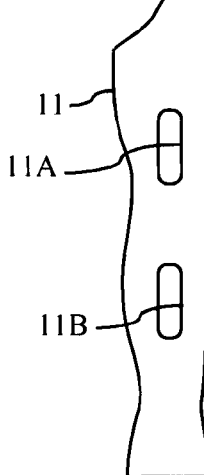
FIG. 10 shows slots provided for movement of the slave piston assembly.

In the withdrawal of the device 10 from the container, the downward pressure is released to decompress the coil spring 33 causing the control bar 17 and the slave piston 26 to move downwards until restricted by slots 11A and 11B, and to lock the control bar and the float 16 against the interior side of the frame section and lock into position (Reference FIG. 11). The fluid level within the tank is determined by viewing the float's "wet line" 16B against the scale 22. FIGS. 2B and 2C show an alternative structure to the slave piston as depicted in FIGS. 7 and 14 and functions in the same manner.

Reference is now made to FIGS. 15-22 where a sampler 90 is shown for collecting a sample or specimen of fluid from the lower region of the tank or container during a depth measurement. The sampler 90 includes a length of tube 80 enclosed at its upper end by a cap 81 threaded thereon, which is removed during the taking of samples. A collar 81A is threaded on the upper end of the tube 80 and in turn threaded onto the lower end the liquid level-measuring device 10 for insertion into the tank or container to obtain a sample of the fluid contained therein. A gasket 81B seals the tube 80 upper end against the leakage of fluid from the tube 80 interior when the cap 81 is in place during storage or transportation of the sampler.

A plug 82 sealingly fits into the plug housing 82. A circular valve seat 92 located on the tube 80 side of the plug housing 82 interconnecting stem 95 which passes through opening 88 to terminate below the tube 80 end in an enlarged head 91. A coil spring 89 received about stem 93 exerts a resilient force against an internal shoulder on the plug housing 82 urging the valve seat 92 into sealing relation against an O-ring 84 on the inwardly facing surface of the of the plug housing 82. A cover plate 85 is secured to the outer end of the threaded tube 80 and includes opening 83 communicating with plug circular seat 92.

In the rest position with the circular seat plug 92 not exposed to depression forces, the valve seat 92 remains closed through the action of spring 89 preventing fluid flow into or out of tube 80.

In assembly, the sampler 90 is removably secured to the lower end portion of the fluid depth-measuring device 10, with the lower ends of each being generally coextensive. Now referring to FIG. 1, the device 10 is shown in the collapsed mode. In order to recover from the extended to the telescopic collapsed mode the snap button 29 protruding from hole 18A of the handle 12 is depressed (Reference FIGS. 2A and 4). The device in then collapsed with the snap ring 29 within the frame 11 being depressed until such time that snap button 29 encounters the hole 18 of the handle 12 and is seated therein. This action securely locks the liquid measuring device for handling or storage.

Referring now to figure FIG. 15, a water level indicator is shown that is used to indicate the water level accumulated at the bottom of a tank or container. The sampling device 25 is identical in construction and function as the liquid level measuring device 10 less the handle 12 and the snap button 29. In use, the water level indicator is attached to the device 10 by threading the water level indicator 25 to the frame section 11. The fully extended liquid level indicator with the attached water indicator 25 in lowered into the tank or container and a downward force is applied to the device. Refer to the prior discussion on the function of device 10 for mechanical operation of the water level indicator.

When a sample is to be taken, the caps 81 and 83 are removed and the entire assembly 90 is inserted into the tank so that the interconnecting stem 95 bears against the tank or container bottom, allowing fluid from the tank or container to move into the tube 90 (arrows) by releasing trap air in the tube 90 through vent hole 9S in the collar 81A. On lifting the measuring device 10 away from the tank or container bottom, the spring 89 causes the circular seat 92 to close against O-ring 84 seated in the top of the plug housing 82 maintaining a sample of the fluid within the tube 90. A second cap 83 is then threaded onto the lower end of the tube 90 and the cap 81 is replaced on the top of the tube 90 to secure the fluid sample against accidental removal and to enable shipment and storage of the sample in the sampler 90. This arrangement is especially advantageous where the sampled fluid is flammable making it undesirable and dangerous to retransfer the fluid to another container. Moreover, the end caps 81 and 83 are provided with seals 81A and 83B, respectively, in order to prevent leakage of the sample fluid and in that way insure safety.

Referring to FIG. 16, a water sampler 25 is shown for indicating the water level accumulated at the bottom of a tank or container during depth measurement. The water indicator 25 includes a frame 26 enclosed at its upper end by a collar 25B threaded thereon. The frame is enclosed with an upper activator module assembly 25A that includes a housing 63. A rotary shaft 62 extending through the housing 63 coupled with torsion spring 57.

What is claimed is:

1. A liquid level measuring device for measuring liquid levels in a container, comprising:

an elongate handle;

an elongate frame arranged in telescoping relationship with the elongate handle, the elongate frame being movable between a collapsed position for storage and an extended position for usage;

a float arranged to be movable lengthwise along the elongate frame, the float having a passage therethrough;

a control rod arranged to extend lengthwise in the elongate frame and to extend through the passage in the float, the control rod being movable between a locked position in which the float is constrained against movement relative to the elongate frame and an unlocked position in which the float is free to move relative to the elongate frame;

a sleeve having a longitudinal generally cylindrical passage therethrough mounted to the control rod;

a pin having an end mounted to the frame and a portion that extends into the passage in the sleeve, the pin and sleeve cooperating to retain the control cocntrol rod in longitudinal alignment with the frame; and an actuator connected to the control rod and arranged to actuate the control rod to move the float from the locked position to the unlocked position in response to a downward pressure between a lower end of the elongate frame and a bottom surface of the container so that the float is free to seek the liquid level in the container and to move the float from the unlocked position back to the locked position when the downward pressure is released, the actuator including an elongate housing having a guide slot formed in a wall portion thereof that makes an angle with the lengthwise axis of the housing, a shaft mounted within the housing and having an end connected to an and of the control rod a guide pin extending from the shaft through the guide slot such that lengthwise movement of the shaft in the housing rotates the shaft and the control rod about their lengthwise axes to move the control rod between the float locked position and the float unlocked position.

2. The liquid level measuring device of claim 1, further comprising means for collecting a sample of the liquid from a container.

3. The liquid level measuring device of claim 1, further comprising a coil spring mounted in the housing around the shaft and arranged to exert a lengthwise force on the shaft so that the control rod is normally in the float locked position.

* * * * *